United States Patent
Park et al.

(10) Patent No.: US 9,593,379 B2
(45) Date of Patent: Mar. 14, 2017

(54) COMPOSITION AND KIT FOR DIAGNOSING BREAST CANCER INCLUDING POLYNUCLEOTIDE WITHIN VESICLE, AND METHOD OF DIAGNOSING BREAST CANCER USING THE SAME

(71) Applicant: Samsung Electronics Co., Ltd., Suwon-si, Gyeonggi-do (KR)

(72) Inventors: Kyung-hee Park, Seoul (KR); Ye-ryoung Yong, Seoul (KR); Hyun-ju Kang, Hwaseong-si (KR); Ga-hee Kim, Yongin-si (KR); Dong-hyun Park, Chuncheon-si (KR); Myo-yong Lee, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 230 days.

(21) Appl. No.: 14/132,964

(22) Filed: Dec. 18, 2013

(65) Prior Publication Data

US 2014/0178885 A1    Jun. 26, 2014

(30) Foreign Application Priority Data

Dec. 18, 2012 (KR) ........................ 10-2012-0148873
Apr. 17, 2013 (KR) ........................ 10-2013-0041965
Jul. 12, 2013 (KR) ........................ 10-2013-0082465

(51) Int. Cl.
*C12Q 1/68*    (2006.01)

(52) U.S. Cl.
CPC ..... *C12Q 1/6886* (2013.01); *C12Q 2600/158* (2013.01); *C12Q 2600/178* (2013.01)

(58) Field of Classification Search
CPC ....................................................... C12Q 1/68
See application file for complete search history.

(56) References Cited

U.S. PATENT DOCUMENTS

| | | | |
|---|---|---|---|
| 8,021,847 B2 | 9/2011 | Pietrzkowski | |
| 8,148,069 B2 * | 4/2012 | Croce | C12N 15/111 |
| | | | 435/6.1 |
| 2010/0151480 A1 | 6/2010 | Taylor et al. | |
| 2010/0298151 A1 | 11/2010 | Taylor et al. | |
| 2011/0003704 A1 | 1/2011 | Skog et al. | |
| 2011/0028332 A1 | 2/2011 | Kuroda et al. | |
| 2011/0112173 A1 | 5/2011 | Brown et al. | |
| 2011/0151460 A1 | 6/2011 | Klass et al. | |
| 2011/0237450 A1 | 9/2011 | Klass et al. | |
| 2012/0295286 A1 | 11/2012 | Berg | |
| 2014/0141986 A1 * | 5/2014 | Spetzler | C12Q 1/6886 |
| | | | 506/9 |

FOREIGN PATENT DOCUMENTS

WO  WO 2009/036236 A1  3/2009
WO  WO 2011/103345 A2  8/2011

OTHER PUBLICATIONS

Taylor et al. (Gynecologic Oncology 110 (2008) 13-21).*
Yao et al. (Cancer Research Jan. 2007, 659-664).*
European Patent Office, Examination Report in European Patent Application No. 13197333.1, Oct. 16, 2015, 8 pp.
Kim et al., Zwitterionic polymer-coated immunobeads for blood-based cancer diagnostics, *Biomaterials*, 35: 294-303 (2014).
European Patent Office, European Search Report in European Patent Application No. 13197333.1, Mar. 7, 2014, 4 pp.
Taylor et al., "MicroRNA signatures of tumor-derived exosomes as diagnostic biomarkers of ovarian cancer", *Gynecologic Oncology*, 110: 13-21 (2008).
Koga et al., "Purification, Characterization and Biological Significance of Tumor-derived Exosomes", *Anticancer Research*, 25; 3703-3708 (2005).
European Patent Office, European Examination Report in European Patent Application No. 13197333.1, Dec. 1, 2014, 7 pp.
Cortez et al., "MicroRNAs in body fluids—the mix of hormones and biomarkers", *Nat. Rev. Clin. Oncol.*, 8(8): 467-477 (2011).

* cited by examiner

*Primary Examiner* — Kimberly Chong
(74) *Attorney, Agent, or Firm* — Leydig, Voit & Mayer, Ltd.

(57) ABSTRACT

A breast cancer diagnostic composition and kit, and methods of diagnosing breast cancer or acquiring information for breast cancer diagnosis by using the composition or kit are provided. The composition or kit includes a polynucleotide that is the same as or complementary to at least one microRNA (miRNA) selected from the group consisting of hsa-miR-126, hsa-miR-23a, hsa-miR-24, hsa-miR-19b, hsa-miR-103, hsa-miR-142-3p, hsa-miR-144, hsa-miR-15a, hsa-miR-185, hsa-miR-93, and hsa-miR-30c in a vesicle, or a fragment of the microRNA.

13 Claims, 6 Drawing Sheets

COMPOSITION AND KIT FOR DIAGNOSING BREAST CANCER INCLUDING POLYNUCLEOTIDE WITHIN VESICLE, AND METHOD OF DIAGNOSING BREAST CANCER USING THE SAME

CROSS-REFERENCE TO RELATED APPLICATIONS

This application claims the benefit of Korean Patent Application No. 10-2012-0148873, filed on Dec. 18, 2012, Korean Patent Application No. 10-2013-0041965, filed on Apr. 17, 2013, and Korean Patent Application No. 10-2013-0082465, filed on Jul. 12, 2013, in the Korean Intellectual Property Office, the disclosures of which are incorporated herein by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 2,606 Byte ASCII (Text) file named "714431_ST25.TXT," created on Dec. 17, 2013.

BACKGROUND

1. Field

The present inventive concept relates to compositions and kits for breast cancer diagnosis, and breast cancer diagnosis methods using the same.

2. Description of the Related Art

Microvesicles are small membranous vesicles that exist in or are secreted from various types of cells. Microvesicles secreted from cells include: (i) exosomes, which are vesicles having a diameter of 30 to 100 nm that originate from cells; (ii) ectosomes (also called shedding microvesicles (SMVs)), which are vesicles that are released directly from plasma membranes and have a diameter of 50 to 1000 nm; and (iii) apoptotic blebs, which are vesicles secreted from dying cells that have a diameter of 50 to 5000 nm.

It has been confirmed by using an electron microscope that exosomes are not directly released from a plasma membrane, but rather originate from specific intracellular regions called multivesicular bodies (MVBs), and are then released into the extracellular environment as exosomes. Although it has not yet been clearly determined which molecular mechanisms are involved in the generation of exosomes, it is known that red blood cells, other various kinds of immune cells, including B-lymphocytes, T-lymphocytes, dendritic cells, blood platelets, and macrophages, and even tumor cells are able to produce and secret exosomes when in a normal live state. Exosomes are also known to be separated and excreted as different cell types depending on whether they are in a normal state, a pathological state, or an abnormal state.

Microvesicles may contain microRNAs (miRNAs), which may be used for detection of the status of individual cells or organisms. The status may be a disease, for example, cancer, hereditary diseases, heart diseases, or neuronal diseases, such as schizophrenia.

Existing breast cancer diagnosis methods are invasive and thus, are painful to patients, and are very costly, which may cause a person to have less frequent checkups. Blood protein markers with high accuracy in blood tests for breast cancer diagnosis are not currently available, and circulating tumor cells (CTCs) are known to be applicable only in diagnosis of metastatic breast cancers, but not in early diagnosis of cancer.

Therefore, for early diagnosis of breast cancer using a less invasive manner, there is a need for selective screening of breast cancer-specific blood markers.

SUMMARY

Provided is a composition and kit for breast cancer diagnosis. The composition and kit comprise (a) at least one polynucleotide having a sequence that is the same as, or complementary to, a microRNA (miRNA) selected from the group consisting of hsa-miR-126, hsa-miR-23a, hsa-miR-24, hsa-miR-19b, hsa-miR-103, hsa-miR-142-3p, hsa-miR-144, hsa-miR-15a, hsa-miR-185, hsa-miR-93, and hsa-miR-30c, or a fragment of the microRNA, wherein the polynucleotide is in a vesicle, and (b) (i) a material specifically binding to the vesicle, (ii) a material capable of intervening into a lipid bilayer of the vesicle, or (iii) a material capable of specifically binding to an integrin protein or a fragment thereof.

Provided is a method of diagnosing breast cancer and acquiring information for breast cancer diagnosis. The methods comprise providing a biological sample comprising a vesicle obtained from a subject; measuring an amount of microRNA in the sample, the microRNA being at least one selected from the group consisting of hsa-miR-126, hsa-miR-23a, hsa-miR-24, hsa-miR-19b, hsa-miR-103, hsa-miR-142-3p, hsa-miR-144, hsa-miR-15a, hsa-miR-185, hsa-miR-93, and hsa-miR-30c; comparing the measured amount of the microRNA with a control; and providing a breast cancer diagnosis based upon the comparison of the amount of the microRNA from the sample with a control, wherein providing a breast cancer diagnosis comprises determining if the measured amount of the microRNA from the biological sample is greater or lesser than the measured amount of the microRNA from the control, wherein when the control is an amount of microRNA from a biological sample from a subject having no breast tumor or a benign breast tumor, an increased amount of microRNA from the biological sample relative to the control is indicative of breast cancer in the subject, and wherein when the control is an amount of microRNA from a biological sample from a subject having breast cancer, a decreased amount of microRNA from the biological sample relative to a control is indicative of non-breast cancer diagnosis.

Additional aspects will be set forth in part in the description which follows and, in part, will be apparent from the description, or may be learned by practice of the presented embodiments.

BRIEF DESCRIPTION OF THE DRAWINGS

These and/or other aspects will become apparent and more readily appreciated from the following description of the embodiments, taken in conjunction with the accompanying drawings of which.

DETAILED DESCRIPTION

Figure 1A:
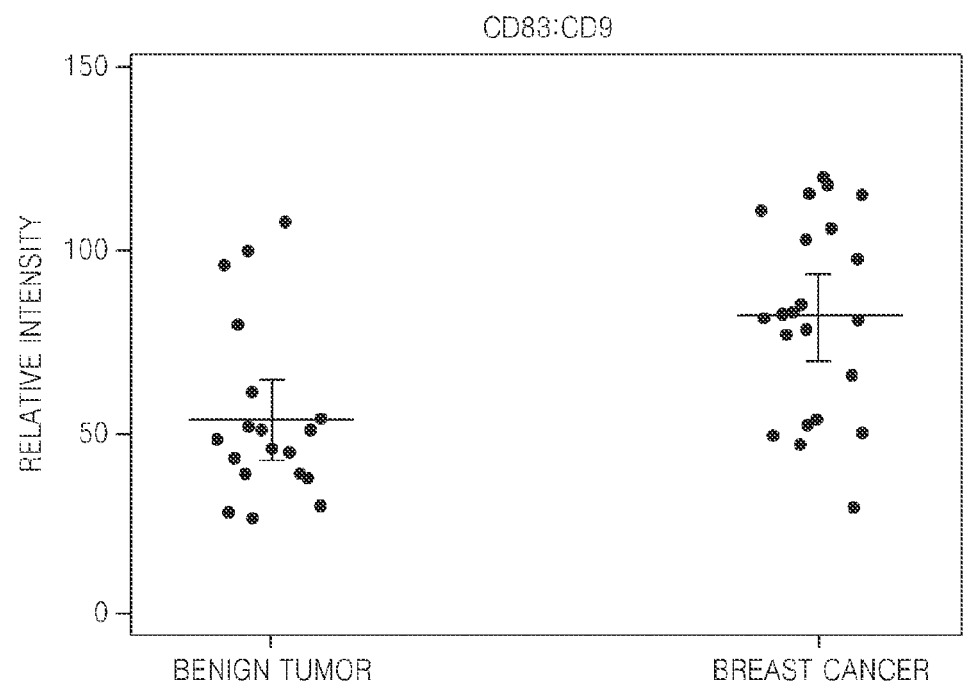
FIGS. 1A-1C are graphs of amounts of microvesicles separated using immunobeads conjugated with anti-CD83 antibody (1A), anti-FASL antibody (1B), or anti-ERBB2 antibody (1C) as a target protein in a benign tumor patient group and a breast cancer patient group. The amount of CD9 protein in the separated microvesicles was determined using an anti-CD9 antibody. The intensity of the microvesicles in arbitrary units (AU) is indicated on the y-axis for each of the benign tumor and breast cancer groups.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

According to an aspect of the present inventive concept, a composition or kit for diagnosing breast cancer comprises at least one polynucleotide having a sequence that is the same as, or complementary to, a microRNA (miRNA) selected from the group consisting of hsa-miR-126, hsa-miR-23a, hsa-miR-24, hsa-miR-19b, hsa-miR-103, hsa-miR-142-3p, hsa-miR-144, hsa-miR-15a, hsa-miR-185, hsa-miR-93, and hsa-miR-30c, or a fragment of the microRNA, wherein the polynucleotide is in a vesicle. The composition can comprise two or more, three or more, four or more, five or more, six or more, seven or more, eight or more, nine or more, ten or more, or eleven vesicles each containing a different polynucleotide having a sequence that is the same as or complementary to a microRNA (miRNA) selected from the group consisting of hsa-miR-126, hsa-miR-23a, hsa-miR-24, hsa-miR-19b, hsa-miR-103, hsa-miR-142-3p, hsa-miR-144, hsa-miR-15a, hsa-miR-185, hsa-miR-93, and hsa-miR-30c, or a fragment of the microRNA. The composition can comprise other additional components, such as other vesicles containing different nucleic acids or other materials.

"Vesicle" refers to a membranous structure that is surrounded by a lipid bilayer. For example, the vesicle may be an exosome or a microvesicle. "Microvesicle" refers to a small vesicle with a membranous structure that originates from a cell. The term "microvesicle" may be interchangeably used herein with the terms "circulating microvesicle" or "microparticle." Microvesicles may exist in cells or may be secreted from cells. Microvesicles secreted from cells may include exosomes, ectosomes (shedding microvesicles (SMVs)), or apoptotic blebs. Exosomes are membranous vesicles of about 30 to about 100 nm diameter that originate from phagocytes. Ectosomes (SMVs) are large membranous vesicles of about 50 to about 1000 nm diameter that are directly released from plasma membranes. Apoptotic blebs are vesicles of about 50 to about 5000 nm diameter that are leaked from dying cells. In vivo microvesicles may contain microRNAs or messenger RNAs (mRNAs). Surface proteins of microvesicles may be disease-specific markers.

MicroRNAs are short ribonucleic acids (RNA) found in eukaryotic cells. MicroRNAs regulate the expression of a gene in the body, are approximately 17 to 25 nucleotides (hereinafter, "nt") in length, and are encoded by DNA. MicroRNAs may increase or reduce the expression of a specific protein after transcription from genomes and fragmentation. Mammalian microRNAs known so far may regulate insulin secretion, lymphocyte differentiation, cell division, cell death, viral replication and the like.

The microRNA in the composition for diagnosing breast cancer may be, for example, hsa-miR-126, hsa-miR-23a, hsa-miR-24, hsa-miR-19b, hsa-miR-103, hsa-miR-142-3p, hsa-miR-144, hsa-miR-15a, hsa-miR-185, hsa-miR-93, hsa-miR-30c, or a combination thereof. The hsa-miR-126, hsa-miR-23a, hsa-miR-24, hsa-miR-19b, hsa-miR-103, hsa-miR-142-3p, hsa-miR-144, hsa-miR-15a, hsa-miR-185, hsa-miR-93, and hsa-miR-30c may be those from *Homo sapiens*, abbreviated as "hsa"). The sequences corresponding to the microRNAs are as follows:

hsa-miR-126 corresponds to the nucleotide sequence of SEQ ID NO. 1;
hsa-miR-23a corresponds to the nucleotide sequence of SEQ ID NO. 2;
hsa-miR-24 corresponds to the nucleotide sequence of SEQ ID NO. 3;
hsa-miR-19b corresponds to the nucleotide sequence of SEQ ID NO. 4;
hsa-miR-103 corresponds to the nucleotide sequence of SEQ ID NO. 5;
hsa-miR-142-3p corresponds to the nucleotide sequence of SEQ ID NO. 6;
hsa-miR-144 corresponds to the nucleotide sequence of SEQ ID NO. 7;
hsa-miR-15a corresponds to the nucleotide sequence of SEQ ID NO. 8;
hsa-miR-185 corresponds to the nucleotide sequence of SEQ ID NO. 9;
hsa-miR-93 corresponds to the nucleotide sequence of SEQ ID NO. 10; and
hsa-miR-30c corresponds to the nucleotide sequence of SEQ ID NO. 11.

The fragment of the microRNA refers to a polynucleotide of microRNA with consecutive nucleotide sequences. The fragment may be, for example, from about 2 nt to 25 nt, 3 nt to 24 nt, 4 nt to 23 nt, 5 nt to 22 nt, 6 nt to 21 nt, 7 nt to 20 nt, 8 nt to 19 nt, 9 nt to 18 nt, 10 nt to 17 nt, 11 nt to 16 nt, 12 nt to 15 nt, or 13 nt to 14 nt in length.

For example, the polynucleotide may have the same nucleotide sequence as that of the microRNA or the fragment thereof. The polynucleotide may have a nucleotide sequence that is complementary to the microRNA or the fragment thereof. The polynucleotide may be a primer or a probe. The polynucleotide may be, for example, 2 nt to 25 nt, 3 nt to 24 nt, 4 nt to 23 nt, 5 nt to 22 nt, 6 nt to 21 nt, 7 nt to 20 nt, 8 nt to 19 nt, 9 nt to 18 nt, 10 nt to 17 nt, 11 nt to 16 nt, 12 nt to 15 nt, or 13 nt to 14 nt in length.

The composition or kit for diagnosing breast cancer may further include a material specifically binding to vesicles, a material capable intervening into the lipid bilayer of vesicles, or a material capable of specifically binding to an integrin protein or a fragment thereof, or a combination thereof. For example, the material specifically binding to vesicles may be a material able to bind to the surface protein, liquid, or sugar of vesicles. The surface protein of vesicles may be, for example, CD83, CD9, EpCAM, caveolin, FasL, HLA-DRA, CD36, CD63, CD81, MUC1, ERBB4, GPER, ERBB2, MLANA, AMHR2, or a combination thereof. The material specifically binding to vesicles may be, for example, a material having a binding affinity to proteins, a substrate for an enzyme, a coenzyme, a regulatory factor, a receptor-specific binding material, lectin, sugar, glucoprotein, an antigen, an antibody or an antigen-binding fragment thereof, a hormone, a neurotransmitter, a phospholiquid-binding protein, a pleckstrin homology (PH) domain-containing protein, a cholesterol-binding protein, or a combination thereof. The antigen-binding fragment may include an antigen-binding site. For example, the antigen-binding fragment may be a single-domain antibody, Fab, Fab', or scFv. The material that can intervene into the lipid bilayer of vesicles may be, for example, a material including a lipophilic moiety, an amphipathic moiety, an amphoteric ion moiety, or a combination thereof. Examples of the lipophilic moiety are fatty acid, sterol, and glyceride. Examples of the amphipathic moiety are phospholipid and sphingolipid. Examples of the amphoteric ion moiety are sulfobetaine, carboxybetaine, and phosphoryl choline. The material specifically binding to vesicles or the material that can intervene into the liquid bilayer of vesicles may be bound with a solid support. Examples of the solid support are polystyrene plate, polystyrene bead, and magnetic bead. The material specifically binding to vesicles may be a material more specifically binding to a vesicle, such as a microvesicle, derived from a breast cancer patient as compared to a vesicle derived from a normal control, such a subject having no breast tumor or a benign breast tumor. The material specifically binding to vesicles may be breast cancer specific microvesicle marker, such as CD83, ERBB2, FASL, or a combination thereof.

The integrin protein is a receptor protein passing through a cell membrane and associated with cell signal transduction, and regulation of cell cycle, cell shape, and cell motility. The integrin protein is a heterodimer consisting of a α subunit and a β subunit. The integrin protein may include an integrin α subunit, an integrin β subunit, or a combination thereof. For example, the integrin protein may include a polypeptide selected from the group consisting of CD49a, CD49b, CD49c, CD49d, CD49e, CD49f, integrin α 8 (ITGA8), integrin α 9 (ITGA9), integrin α 10 (ITGA10), integrin α 11 (ITGA11), CD11D, CD103, CD11a, CD11 b, CD51, CD41, CD11c, CD29, CD18, CD61, CD104, integrin β 5 (ITGB5), integrin β 6 (ITGB6), integrin β 7 (ITGB7), and integrin β 8 (ITGB8). A fragment of the integrin protein refers to a polypeptide having consecutive amino acids sequence of the integrin protein.

The material capable of specifically binding to the integrin protein or a fragment thereof may be an antibody specifically binding to the integrin protein. The antibody specifically binding to the integrin protein may be a monoclonal antibody or polyclonal antibody. The antibody specifically binding to the integrin protein may be a full-length antibody or an antigen-binding fragment. The antigen-binding fragment, which includes an antigen-binding region, may be, for example, a single-domain antibody, Fab, Fab', or scFv. The antibody specifically binding to the integrin protein may be an anti-integrin α subunit antibody or an anti-integrin β subunit antibody.

According to another aspect of the present inventive concept, a method of diagnosing breast cancer includes: providing a biological sample comprising a vesicle obtained from a subject; measuring an amount of microRNA in the sample, the microRNA being at least one selected from the group consisting of hsa-miR-126, hsa-miR-23a, hsa-miR-24, hsa-miR-19b, hsa-miR-103, hsa-miR-142-3p, hsa-miR-144, hsa-miR-15a, hsa-miR-185, hsa-miR-93, and hsa-miR-30c; comparing the measured amount of the microRNA with a control (e.g., a measured amount of microRNA in a vesicle separated from a positive or negative control sample, or data representing the amount of microRNA in a positive or negative control sample); and providing a breast cancer diagnosis based upon the comparison of the amount of the microRNA from the sample with the control.

The method may include providing the biological sample comprising a vesicle obtained from a subject, and measuring the amount of microRNAs in the sample, wherein the microRNA include two or more, three or more, four or more, five or more, six or more, seven or more, eight or more, nine or more, ten or more, or all eleven microRNAs of the group consisting of hsa-miR-126, hsa-miR-23a, hsa-miR-24, hsa-miR-19b, hsa-miR-103, hsa-miR-142-3p, hsa-miR-144, hsa-miR-15a, hsa-miR-185, hsa-miR-93, and hsa-miR-30c.

The method of diagnosing breast cancer includes providing a biological sample taken from a subject.

The subject may be a mammal, including a mouse, rat, guinea pig, hamster, cat, dog, pig, cow, horse, or primate (e.g., human).

The biological sample may be, for example, urine, mucus, saliva, tears, blood plasma, blood serum, sputum, spinal fluid, serous fluid from a pleural cavity, nipple aspirate, lymph, tracheolar fluid, intestinal juice, genitourinary tract fluid, breast milk, semen, peritoneal fluid, cystic tumor fluid, amniotic fluid, or any combination thereof. The biological sample may contain a vesicle or be vesicle itself.

Providing a biological sample may include blood collecting, sampling, biopsy, separating, or isolating the sample from the individual. Providing a biological sample may include separating or isolating vesicles from the sample. Separating the vesicle from the biological sample may be performed, for example, using a solid support or a centrifugal force, a density gradient method, ultracentrifugation, filtration, dialysis, immunoaffinity chromatography using antibodies, free-flow electrophoresis, or a combination thereof. Separating the vesicle from the biological sample may include incubating the vesicle together with, for example, a material specifically binding to the vesicle or a material that can intervene into the lipid bilayer of the vesicle. The incubating may be performed in vitro. In some embodiments, the separating of the vesicle from the biological sample may include washing.

The amount of the microRNA may be measured using primers or a probe of a polynucleotide that is the same as or complementary to at least one microRNA (miRNA) selected from the group consisting of hsa-miR-126, hsa-miR-23a, hsa-miR-24, hsa-miR-19b, hsa-miR-103, hsa-miR-142-3p, hsa-miR-144, hsa-miR-15a, hsa-miR-185, hsa-miR-93, and hsa-miR-30c in a vesicle or a fragment of the microRNA. The polynucleotide may be, for example, 2 nt to 25 nt, 3 nt to 24 nt, 4 nt to 23 nt, 5 nt to 22 nt, 6 nt to 21 nt, 7 nt to 20 nt, 8 nt to 19 nt, 9 nt to 18 nt, 10 nt to 17 nt, 11 nt to 16 nt, 12 nt to 15 nt, or 13 nt to 14 nt in length. The amount of the microRNA may be measured using, for example, a quantitative reverse transcription-polymerase chain reaction (qRT-PCR).

The method of diagnosing breast cancer or acquiring information required for breast cancer diagnosis may include comparing the measured amount of the microRNA in biological sample with a control (e.g., a measured amount of microRNA in a vesicle of a reference (control) sample).

The control sample may be a sample obtained from a normal or benign tumor patient (negative control). Alternatively, the control sample may be a sample obtained from a breast cancer patient (positive control). The control may also be provided by data representative of the amount of miRNA in a pool of normal or benign patients, or breast cancer positive patients.

The method of diagnosing breast cancer may include providing a breast cancer diagnosis based upon the comparison of the amount of the microRNA from the sample with a control. Providing a breast cancer diagnosis may include determining whether the measured amount of the microRNA from the biological sample is greater or lesser than the amount of the microRNA from the control. For example, an increased amount of microRNA from the biological sample relative to a negative control sample is indicative of breast cancer in the subject. The negative control may be an amount of microRNA from a biological sample from a subject having no breast tumor or a benign breast tumor. The increased amount of microRNA from the biological sample relative to the negative control may be an increase by more than about 0.2, 0.4, 0.5, 0.6, 0.8, 1.0, 1.2, 1.4, 1.6, 1.8, 2.0, 2.2, 2.4, 2.6, or 2.8 Cp units.

A decreased amount of microRNA from the biological sample (e.g., vesicle itself) relative to the amount of microRNA in a positive control sample is indicative of a diagnosis of non-breast cancer in the subject. The positive control may be an amount of microRNA from a biological sample from a subject having breast cancer. The decreased amount of microRNA from the biological sample relative to the positive control may be a decrease by more than about 0.2, 0.4, 0.5, 0.6, 0.8, 1.0, 1.2, 1.4, 1.6, 1.8, 2.0, 2.2, 2.4, 2.6, or 2.8 Cp units.

The method of diagnosing breast cancer or acquiring information required for breast cancer diagnosis may further include: measuring an amount of an integrin protein in the biological sample (e.g., vesicles); comparing the amount of the integrin protein with a control (e.g., a measured amount of an integrin protein in a vesicle separated from the positive or negative control; or data reflecting the level of integrin present in the positive or negative control patient sample or pool of such samples). The method further comprises determining that the subject is a breast cancer patient or has a high possibility of having breast cancer when the amount of the integrin protein in the vesicle from the biological sample is greater than the negative control or less than the positive control.

The amount of the integrin protein may be measured using electrophoresis, western blotting, enzyme-linked immunosorbent assay (ELISA), a protein chip, a mass spectrometer, or a combination thereof.

The method of diagnosing breast cancer or acquiring information required for breast cancer diagnosis may be an in vitro method. The method of diagnosing breast cancer may further include administering one or more drugs for treating a breast cancer to a subject diagnosed as having a breast cancer or higher possibility of having a breast cancer according to the method of diagnosing breast cancer to treat a breast cancer. The drugs may be an anti-cancer drug specific for breast cancer, or a combination with other cancer drugs.

The method of diagnosing breast cancer or acquiring information required for breast cancer diagnosis may include dissolving the biological sample (e.g., vesicle), for example, in a solvent containing, for example, a chaotropic salt, an organic solvent, or a surfactant. The dissolving of the biological sample may be performed, for example, by heating, stirring, rotating, vortexing, or a combination thereof.

One or more embodiments will now be described in more detail with reference to the following examples. However, these examples are for illustrative purposes only and are not intended to limit the scope of the one or more embodiments.

Example 1

Breast Cancer Specific Protein and microRNA Markers (1) Screening of Surface Protein Markers of Breast Cancer-Related Microvesicles 8 ml to 10 ml of blood was sampled from 20 benign tumor patients (as non-breast cancer patients) and 22 breast cancer patients (breast cancer, $2^{nd}$ stage Luminal B type) into BD Vacutainer® Plus plastic whole blood tube. Plasma was separated from each blood sample by centrifuging the sample at 1300×g for 10 minutes at 4° C., and then stored −80° C. until use. Before use, the plasma was thawed and centrifuged at about 3,000×g for 5 minutes at about 4° C. to remove plasma lipids and cell debris, thus supernatant was used in the following experiment.

The obtained plasma was pooled and diluted using a PBS buffer having 3 times the volume of the plasma sample. The diluted plasma was sequentially centrifuged at 2,000×g for 30 minutes at 4° C. and at 12,000×g for 30 minutes at 4° C. Pallets were removed from the centrifuged result, and a supernatant was filtered by using a 0.22 μm filter. The filtered solution was concentrated by using a 300 kDa cut-off membrane column (Vivaproducts) and ultrahigh-speed centrifuged at 110,000×g for 2 hours at 4° C. to obtain microvesicles as its precipitates.

In order to identify whether an amount of the CD83, ERBB2, and FASL proteins in the microvesicles increased or decreased in a breast cancer patient compared to a normal person, an amount of CD9, which is a microvesicle marker as a internal control group was measured. The obtained precipitates, i.e., the microvesicles, were suspended in PBS, a lysis buffer and NuPAGE LDS sample buffer (Life Technologies) at pH of 8.4 including lithium dodecyl sulfate was added into the tube, and the microvesicles underwent lysis by heat treating the resultant in a heating block at 95° C. for 10 minutes. The electrophoresis was performed on the lysate, and immunoblotting was performed thereon. The detection from the immunoblotting was performed by using a rabbit anti-CD83 antibody (BD Pharminen), an rabbit anti-ERBB2 antibody (R&D Systems), an rabbit anti-FASL antibody (BD Pharmingen), and a rabbit anti-CD9 antibody (Novus Biologicals) as a primary antibody and an HRP-conjugated anti-rabbit antibody as a secondary antibody, and the light-emitting image was analyzed by using Las min 4000. In the results of analysis of the immunoblotting, the CD83, ERBB2, and FASL proteins were demonstrated a significant difference in amounts between the benign tumor patient group and the breast cancer patient group based on the results of immunoblotting on the microvesicles from the two patient groups.

Therefore, breast cancer specific microvesicles can be separated using an anti-CD83 antibody (BD Pharmingen), an anti-ERBB2 antibody (R&D Systems), or an anti-FASL antibody (BD Pharmingen) from the blood.

(2) Verification of Surface Protein Marker

To determine an amount of CD83, ERBB2, or FASL proteins-expressed microvesicles obtained from each of the benign tumor patients and breast cancer patients, microvesicles were separated from the plasma of Example 1(1) using immunobeads conjugated with anti-CD83 antibody, anti-CD83 antibody or anti-CD83 antibody and the amount of separated microvesicles was determined by immunoblotting using an anti-CD9 antibody specific binding to CD9 protein (a microvesicle marker).

100 mL of Dynabeads® M-270 amine solution (Life Technologies) was placed into an Eppendorf tube and washed with MES buffer containing NaCl (pH 6.0). A polyacryl acid (PAA) (Aldrich) solution was prepared in MES buffer, and EDC and NHS as coupling agents were added to the solution. The beads were then reacted at RT, were washed with MES buffer (pH 6.0), and then resuspended in MES buffer containing EDC and NHS. Then, the beads were washed with MES buffer and reacted with protein G solution in MES buffer. After the reaction, 1.2 mg of sulfobetaine (Aldrich) was added to the solution and incubated. After incubation, the beads were washed with PBST and PBS. Anti-CD83 stock solution was prepared in PBS solution (pH 7.4) and diluted with NaOAc (pH 5.0). The beads that bound protein G were incubated with 80 mg of anti-CD83 solution. The beads were then washed with sodium borate buffer (pH 9.3), and the antibody was cross-linked to protein G using dimethyl pimelimidate dihydrochloride dissolved in sodium borate buffer (pH 9.3). The reaction was terminated by washing and incubating the immunobeads with ethanolamine. After the incubation, the immunobeads were washed with PBST and PBS. The prepared immunobeads were washed with PBS and stored in PBS at 4° C. until use.

After blood was sampled from 30 benign tumor patients (as non-breast cancer patients) and 30 breast cancer patients (breast cancer, $2^{nd}$ stage, Luminal B type), plasma was separated from each blood sample as described in section (1), and used without pooling.

300 μl of each plasma sample was mixed with 30 μl (antibody 0.8 μg/1 μl beads) of the beads coated with the anti-CD83 antibody in a test tube (Axygen), and incubated at room temperature for about 4 hours while rotating with a Grant Bio Rotator. After the supernatant was removed from the reaction mixture, the beads were washed with PBS. The beads were then resuspended in PBS and incubated at 30 rpm and RT for another 3 hours. After the supernatant was removed, the beads were resuspended in LDS loading buffer (Invitrogen) and boiled at 100° C. for 10 min. The amount of CD9 protein was assessed by immunoblotting assays as described in section (1). The difference in the amount of CD9 protein expressed in the antibody-separated microvesicles between the two groups was determined by the non-parametric, Wilcoxon rank sum test. Test results of the Wilcoxon rank sum test at a p-value of less than 0.05 are considered statistically significant.

Figure 1B:
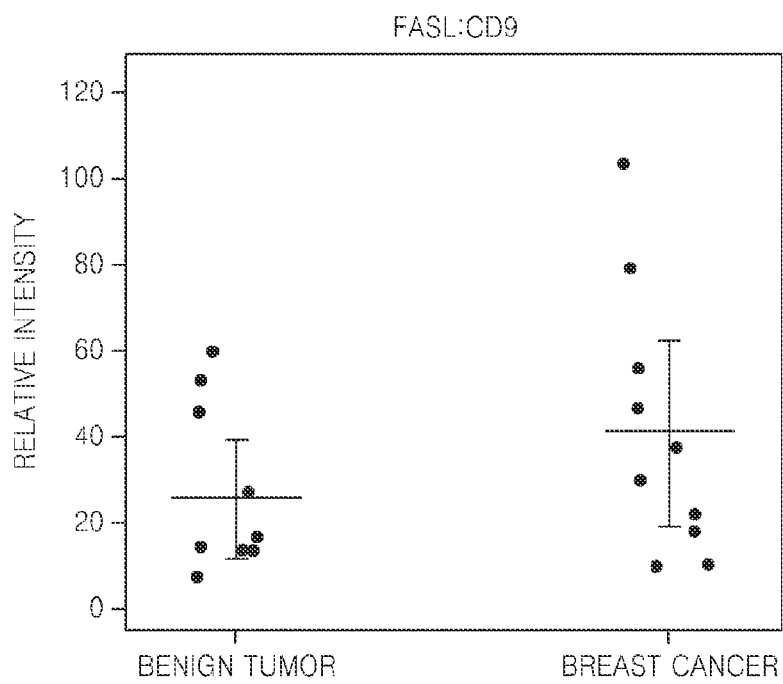
Figure 1C:
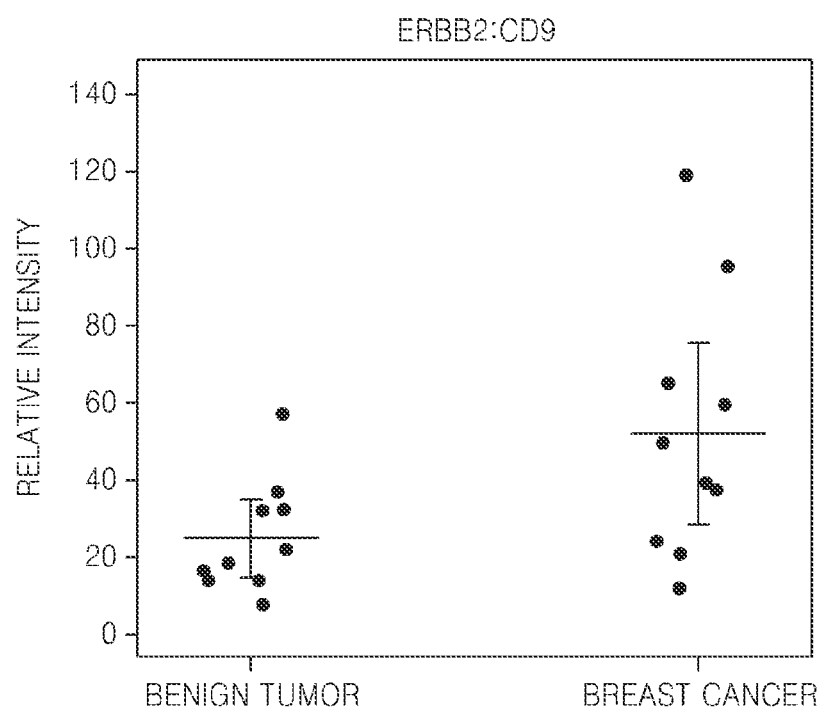

Referring to FIGS. 1A-1C, when the microvesicles were separated using the anti-CD83 antibody (BD Pharmingen), the anti-ERBB2 antibody (R&D Systems), or the anti-FASL antibody (BD Pharmingen) and then the amount of the CD9 protein in the separated microvesicles was determined using the anti-CD9 antibody (R&D Systems), a statistically significant difference in the amount of the microvesicles obtained was found between the benign tumor patient group and the breast cancer patient group. This result indicates that the CD83, ERBB2 and FASL proteins were expressed or displayed on the surfaces of the microvesicles, and that the CD83 proteins were concentrated more in breast cancer-related microvesicles than the benign tumor patient group.

(3) Screening of microRNA Markers for Breast Cancer-Related Microvesicles

Microvesicles were separated from the plasma using the immunobead conjugated with the anti-CD83 antibody as described in section (2), and miRNA from the separated microvesicles were extracted by using the miRNeasy Mini kit (Qiagen) according to the manufacturer's protocol.

Figure 2A:
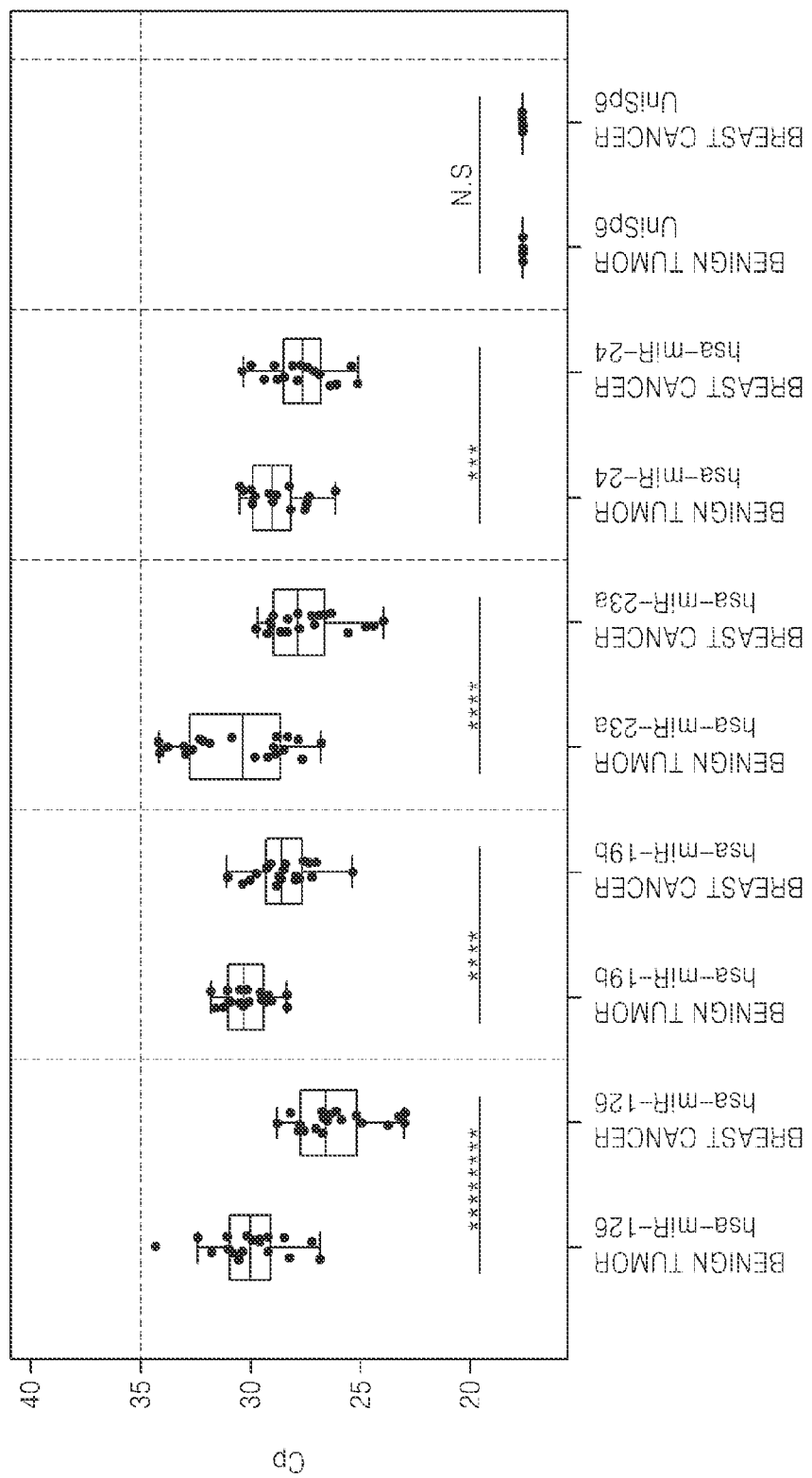
FIGS. 2A and 2B are comparative graphs of amounts of microRNA in the benign tumor patient group and the breast cancer patient group. Crossing-point (Cp) values (i.e., cycles) are indicated on the y-axis for samples of microRNAs indicated on the x-axis.
Figure 2B:
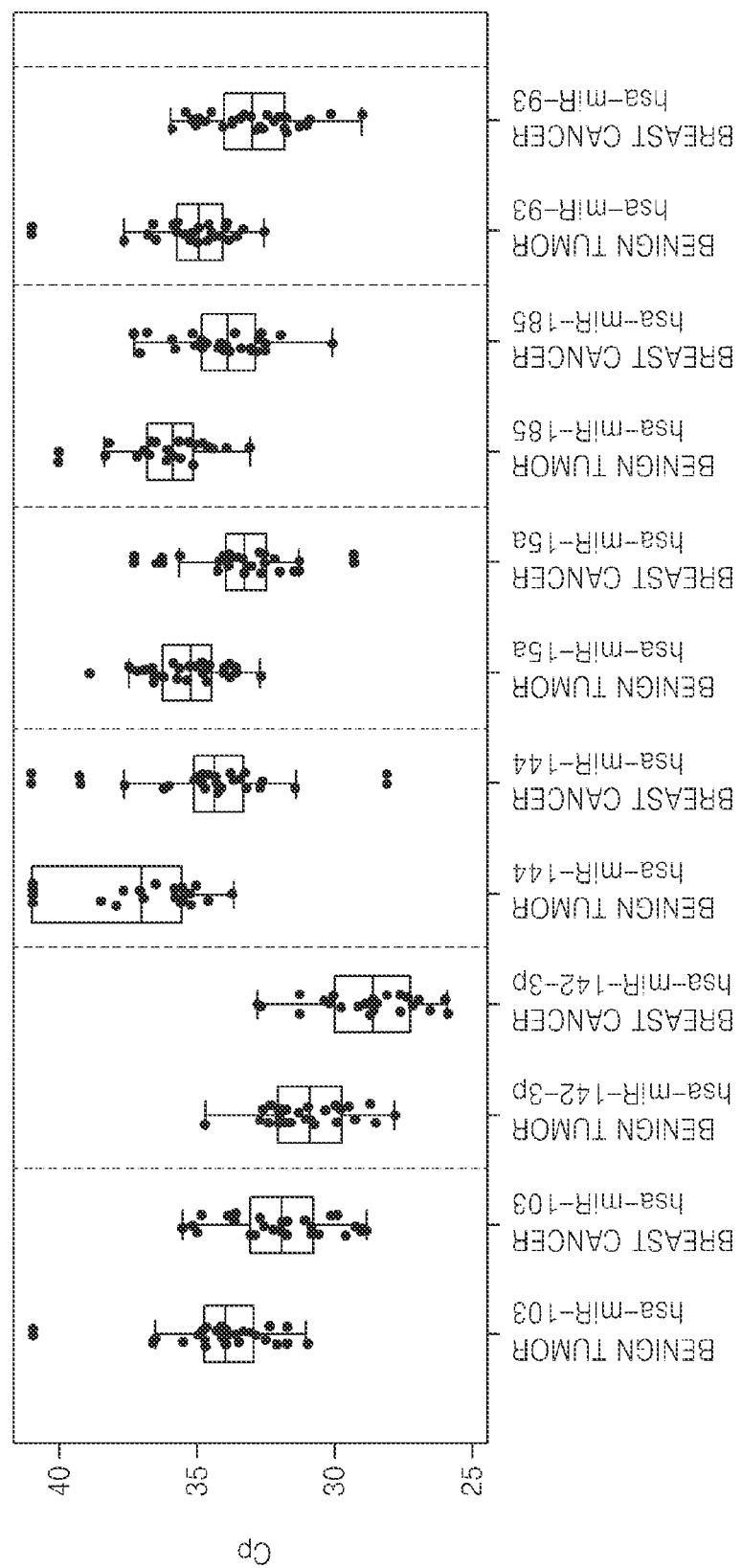

The separated RNA was reverse transcribed to cDNA by using the Universal cDNA synthesis kit (Exiqon). All RT products were combined with SYBR Green master mix in a final volume of 4 mL. The mixture was loaded into the 384-well plate of the microRNA Ready-to-Use PCR human panel I V2.R. Quantitative reverse transcription-polymerase chain reactions (qRT-PCRs) also were performed using mercury LNA Universal RT microRNA PCR (Exiqon). Real-time PCR was conducted using the LightCycler 480 Real-Time PCR System (Roche) according to the manufacturer's instructions: 95° C. for 10 min, followed by total 45 cycles of 95° C. for 10 sec and 60° C. for 1 min. The amounts of measured miRNA represented by crossing point (Cp) in individual patients were corrected based on qRT-PCR control for comparison. The results of the qRT-PCR are shown in FIGS. 2A and 2B. The results of analysis of the qRT-PCR results are shown in Table 1 below.

TABLE 1

| Microvesicle surface protein | MicroRNA | Amount of microRNA in benign tumor patient group (Cp) | Amount of microRNA in breast cancer patient group (Cp) | Difference in microRNA amount (ΔCp) | p-value |
| --- | --- | --- | --- | --- | --- |
| CD83 | hsa-miR-126 | 30 | 26.3 | −3.7 | 1.36E−08 |
| | hsa-miR-23a | 30.6 | 27.5 | −3.1 | 1.41E−04 |
| | hsa-miR-24 | 32 | 30.1 | −1.9 | 2.98E−07 |
| | hsa-miR-19b | 30.1 | 28.5 | −1.6 | 8.61E−05 |
| | hsa-miR-103 | 34.2 | 31.9 | −2.3 | 1.39E−04 |
| | hsa-miR-142-3p | 30.8 | 28.7 | −2.1 | 4.03E−05 |
| | hsa-miR-144 | 37.5 | 34.6 | −2.9 | 8.23E−06 |
| | hsa-miR-15a | 35.3 | 33.3 | −2 | 1.20E−05 |
| | hsa-miR-185 | 36.1 | 34 | −2.1 | 2.18E−05 |
| | hsa-miR-93 | 35.1 | 32.9 | −2.2 | 1.65E−05 |
| | hsa-miR-30c | 33.9 | 32 | −1.9 | 6.01E−06 |

In FIGS. 2A and 2B and Table 1, a smaller Cp level indicates a higher miRNA expression. The differences in amount of microRNA between the two patient groups were analyzed using the Wilcoxon rank sum test. Results with a p-value of less than 0.05 are considered statistically significant.

Referring to FIGS. 2A and 2B and Table 1, hsa-miR-126, hsa-miR-23a, hsa-miR-24, hsa-miR-19b, hsa-miR-103, hsa-miR-142-3p, hsa-miR-144, hsa-miR-15a, hsa-miR-185, hsa-miR-93, and hsa-miR-30c were found as markers of breast cancer-related microvesicles as indicated below.

hsa-miR-126;  5'-UCGUACCGUGAGUAAUAAUGCG-3'  (SEQ ID NO. 1)

hsa-miR-23a;  5'-AUCACAUUGCCAGGGAUUUCC-3'  (SEQ ID NO. 2)

hsa-miR-24;   5'-UGGCUCAGUUCAGCAGGAACAG-3'  (SEQ ID NO. 3)

hsa-miR-19b;  5'-UGUGCAAAUCCAUGCAAAACUGA-3'  (SEQ ID NO. 4)

hsa-miR-103;  5'-AGCAGCAUUGUACAGGGCUAUGA-3'  (SEQ ID NO. 5)

hsa-miR-142-3p; 5'-UGUAGUGUUUCCUACUUUAUGGA-3'  (SEQ ID NO. 6)

hsa-miR-144;  5'-UACAGUAUAGAUGAUGUACU-3'  (SEQ ID NO. 7)

hsa-miR-15a;  5'-UAGCAGCACAUAAUGGUUUGUG-3'  (SEQ ID NO. 8)

hsa-miR-185;  5'-UGGAGAGAAAGGCAGUUCCUGA-3'  (SEQ ID NO. 9)

hsa-miR-93;   5'-CAAAGUGCUGUUCGUGCAGGUAG-3'  (SEQ ID NO. 10)

hsa-miR-30c;  5'-UGUAAACAUCCUACACUCUCAGC-3'  (SEQ ID NO. 11)

(4) Diagnostic Accuracy Evaluation of Surface Protein and microRNA in Breast Cancer-Related Microvesicles Estimation accuracy, an area under the curve (AUC), and a p-value in the breast cancer diagnosis based on amounts of surface protein CD83 and microRNA in microvesicles as described in sections (2) and (3) were calculated using the samples from 20 benign tumor patients and 22 breast cancer patients. The results are shown in Table 2 below. Estimation accuracy means how well the assumption that a patient has breast cancer or benign tumor matches with the actual fact that a patient has breast cancer or a benign tumor. An AUC of 0.8 or greater is considered to provide better effects.

TABLE 2

| Microvesicle surface protein | Type of variable | Number of variables | Discriminant (Logistic regression analysis) | Estimation accuracy | AUC |
| --- | --- | --- | --- | --- | --- |
| CD83 | Clinical information | 1 | Age | 0.62 | 0.62 |
|  | Microvesicle surface protein | 1 | CD9 | 0.76 | 0.76 |
|  | Microvesicle miRNA | 4 | hsa-miR-126 + hsa-miR-19b + hsa-miR-23a + hsa-miR-24 | 0.93 | 0.93 |
|  | MicroRNA | 1 | hsa-miR-126 | 0.86 | 0.85 |
|  | MicroRNA | 1 | hsa-miR-19b | 0.71 | 0.71 |
|  | MicroRNA | 1 | hsa-miR-23a | 0.71 | 0.71 |
|  | MicroRNA | 1 | hsa-miR-24 | 0.845 | 0.845 |
|  | MicroRNA | 1 | hsa-miR-103 | 0.741 | 0.741 |
|  | MicroRNA | 1 | hsa-miR-142-3p | 0.741 | 0.741 |
|  | MicroRNA | 1 | hsa-miR-144 | 0.69 | 0.69 |
|  | MicroRNA | 1 | hsa-miR-15a | 0.81 | 0.81 |
|  | MicroRNA | 1 | hsa-miR-185 | 0.776 | 0.776 |
|  | MicroRNA | 1 | hsa-miR-93 | 0.759 | 0.759 |
|  | MicroRNA | 1 | hsa-miR-30c | 0.776 | 0.776 |

Referring to Table 2 above, a benign tumor and breast cancer may be distinguishable from one another with 86% accuracy based on the amounts of hsa-miR-126 in the microvesicles with the surface protein CD83 separated from plasma. Accuracy in estimation using hsa-miR-126 was higher by about 24%, as compared with estimation using clinical information (age) and by about 10% as compared with estimation based on an amount of the surface protein CD9.

Example 2

Breast Cancer Specific Protein Integrin-β and microRNA Markers (1) Quantification of Integrin-β Protein in Microvesicles and Analysis of Receiver Operating Characteristics (ROC)

The microvesicles separated from the plasma were resuspended in LDS loading buffer (Invitrogen) as described in section (2) of Example 1, heated at about 100° C. for about 10 minutes to lyze the microvesicles bound to the immunobeads. The lysate of the microvesicle was subject to electrophoresis to analyze the proteins from the microvesicles bound to the immunobeads conjugated with anti-CD83 antibody.

The gels resulting from electrophoresis were transferred to polyvinylidene difluoride (PVDF) membranes, which were then immersed in 10 ml of a mixture of Tris-Buffered Saline and Tween 20) (TBST) (including 1% skimmed milk powder) including 1 µl of anti-integrin-β antibody (R&D systems), or 10 ml of TBST (including 1% skimmed milk powder) including 1 µl of anti-CD9 antibody (R&D systems), and incubated at room temperature for about 1 hour, followed by washing with 20 ml of TBST three times, each for 5 minutes. The resulting washed membranes were incubated in the same manner as above with a secondary antibody bound with horseradish peroxidase (HRP), and then washed with 20 ml of TBST three times, each for 5 minutes.

The washed membranes were incubated in 2 ml of a SuperSignal West Femto Maximum Sensitivity substrate (Pierce) at room temperature for about 5 minutes, and then imaged using a LAS imaging system (Fujifilm) to detect bands of integrin-β and CD9, followed by analysis using Image J software (NCI) to measure background and band intensities of integrin-β and CD9.

Figure 3A:
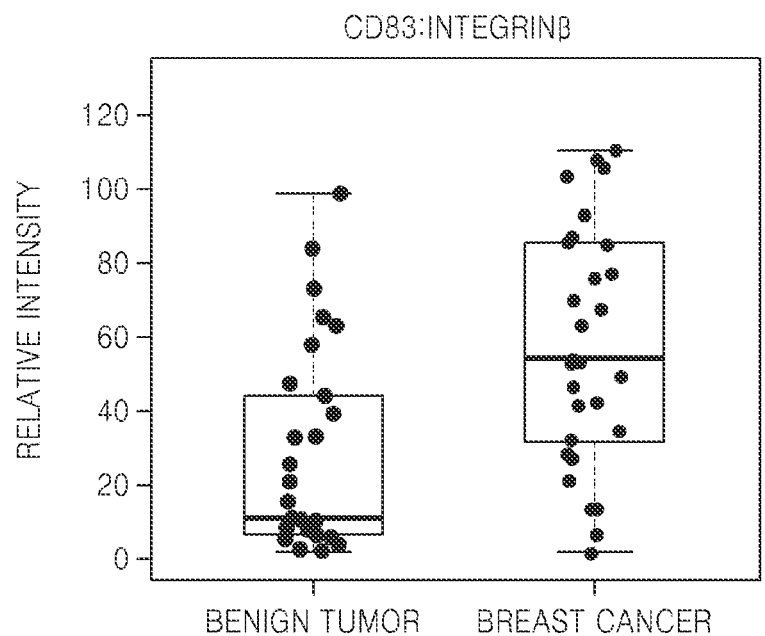
FIGS. 3A-3C are graphs showing relative intensities of integrin-β protein band obtained by immunoblotting of the microvesicle separated from the benign tumor patient group and the breast cancer patient group using by immunobeads conjugated with anti-CD83 antibody (3A), anti-FASL antibody (3B), or anti-ERBB2 antibody (3C)
Figure 3B:
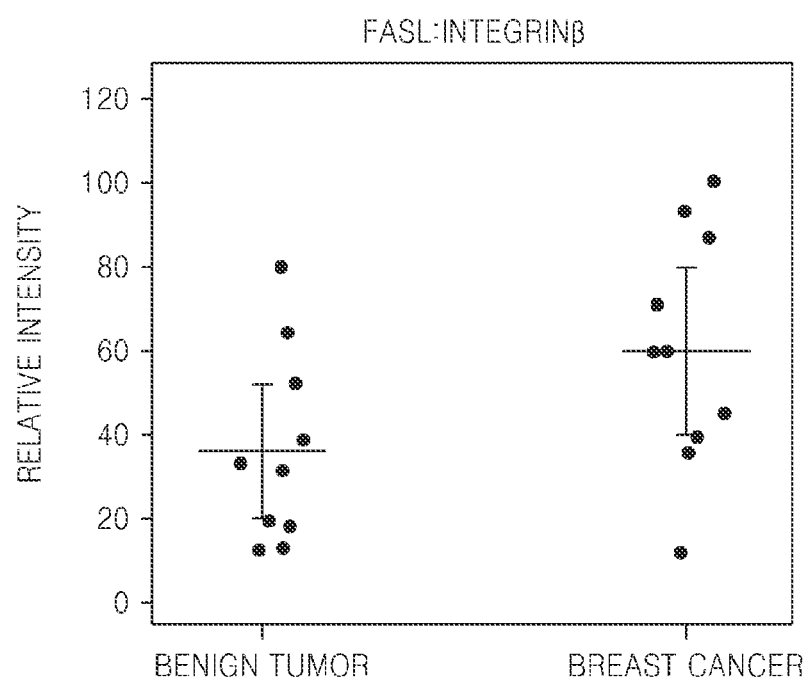
Figure 3C:
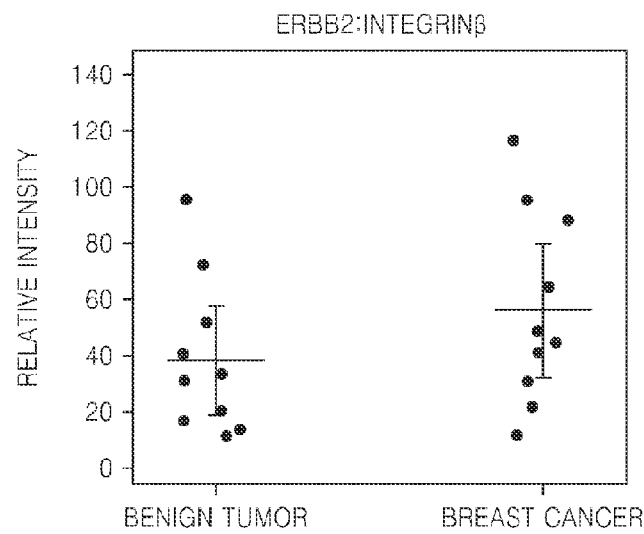

Relative intensities of integrin-β protein band obtained by immunoblotting of the microvesicle separated from the benign tumor patient group and the breast cancer patient group using by immunobeads conjugated with anti-CD83 antibody, anti-FASL antibody, or anti-ERBB2 antibody are shown in FIGS. 3A-3C, respectively (30 benign tumor patients and 30 breast cancer patients). Referring to FIGS. 3A-3C, the breast cancer patients were found to have a significantly increased amount of integrin-β protein in microvesicles, compared to the benign tumor patients.

A receiver operating characteristic (ROC) curve was analyzed based on the integrin-β band intensities (y-axis: sensitivity, x-axis: 1-specificity). The results are shown in FIG. 3B. Area under the curves (AUCs) obtained from the ROC curves are shown in Table 3.

TABLE 3

|       | CD9   | integrin-β |
|-------|-------|------------|
| CD83  | 0.760 | 0.690      |
| FASL  | 0.600 | 0.650      |
| ERBB2 | 0.750 | 0.600      |

(2) Combined AUC of Integrin-β and microRNA

Logistic regression analysis was performed using the Cp values from the qRT-PCR of section (3) of Example 1 and the measured integrin-β band intensities obtained by immunoblotting of the microvesicle separated by immunobeads conjugated with anti-CD83 antibody in section (1) of Example 2 as parameters to obtain a combined AUC of integrin-β and microRNA.

Figure 4:
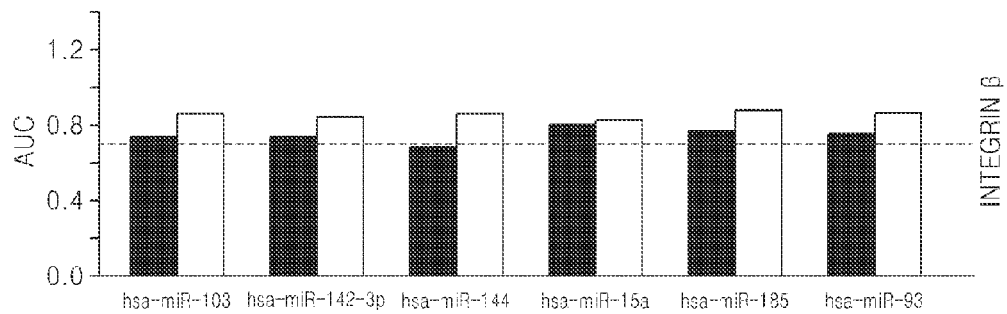
FIG. 4 is a graph of area under the curves (AUCs) of integrin-β and microRNA in microvesicles separated from the benign tumor patient group and the breast cancer patient group, and combined AUCs of integrin-β and microRNA. The dashed line indicates the AUCs of integrin-β, black bars indicated AUCs of microRNA, and white bars indicate combined AUCs of integrin-β and microRNA.

The results are shown in FIG. 4 and Table 4 below.

TABLE 4

|              | AUC   | combined AUCs of integrin-β and microRNA |
|--------------|-------|------------------------------------------|
| hsa-miR-103  | 0.741 | 0.862                                    |
| hsa-miR-142-3p | 0.741 | 0.845                                  |
| hsa-miR-144  | 0.69  | 0.862                                    |
| hsa-miR-15a  | 0.81  | 0.828                                    |
| hsa-miR-185  | 0.776 | 0.879                                    |
| hsa-miR-93   | 0.759 | 0.862                                    |
| integrin-β   | 0.690 |                                          |

Referring to FIG. 4, dashed lines indicate AUCs of integrin-β, black bars indicate AUCs of microRNA, and white bars indicate combined AUCs of integrin-β and microRNA.

Referring to FIG. 4 and Table 4, the combined AUCs of integrin-β and microRNA were more than the AUCs of integrin-β by about 0.189 on average and more than AUCs of microRNA by about 0.172 on average, indicating that combination of integrin-β and microRNA may improve diagnostic accuracy of breast cancer.

As described above, according to the one or more of the above embodiments of the present inventive concept, use of a breast cancer diagnostic composition and kit, each including a polynucleotide that is the same as or complementary to at least one microRNA selected from the group consisting of hsa-miR-126, hsa-miR-23a, hsa-miR-24, hsa-miR-19b, hsa-miR-103, hsa-miR-142-3p, hsa-miR-144, hsa-miR-15a, hsa-miR-185, hsa-miR-93, and hsa-miR-30c in a vesicle or a fragment of the microRNA, and methods for diagnosing breast cancer or acquiring information for breast cancer diagnosis using the composition or kit may allow early diagnosis of breast cancer using a less invasive manner, and thus may be more convenient for patients.

It should be understood that the exemplary embodiments described herein should be considered in a descriptive sense only and not for purposes of limitation. Descriptions of features or aspects within each embodiment should typically be considered as available for other similar features or aspects in other embodiments.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of diagnosing breast cancer, the method comprising:
   providing a biological sample comprising a vesicle obtained from a subject;
   incubating the biological sample with an antibody or antigen binding fragment thereof that specifically binds to a surface protein of the vesicle, wherein the surface protein is CD83, CD9, EpCAM, caveolin, FasL, HLA-DRA, CD36, CD63, CD81, MUC1, ERBB4, GPER, ERBB2, MILANA, AMHR2, or a combination thereof;
   isolating the antibody or antigen binding fragment thereof bound vesicle from the biological sample;
   measuring an amount of microRNA (miRNA) in the isolated vesicle, the microRNA being at least one selected from the group consisting of hsa-miR-126, hsa-miR-23a, hsa-miR-24, hsa-miR-19b, hsa-miR-103, hsa-miR-142-3p, hsa-miR-144, hsa-miR-15a, hsa-miR-185, and hsa-miR-93;
   comparing the measured amount of the microRNA with a control; and
   providing a breast cancer diagnosis based upon the comparison of the amount of the microRNA from the sample with a control,
   wherein providing a breast cancer diagnosis comprises determining if the measured amount of the microRNA from the biological sample is greater or lesser than the measured amount of the microRNA from the control,
   wherein when the control is an amount of microRNA from a biological sample from a subject having no breast tumor or a benign breast tumor, an increased amount of microRNA from the biological sample relative to the control is indicative of breast cancer in the subject, and
   wherein when the control is an amount of microRNA from a biological sample from a subject having breast cancer, a decreased amount of microRNA from the biological sample relative to a control is indicative of non-breast cancer diagnosis.

2. The method of claim 1, wherein the increased or decreased amount of microRNA from the biological sample relative to the control is an increase or decrease by more than about 0.5 Cp value.

3. The method of claim 1, wherein the biological sample is urine, mucus, saliva, tears, blood plasma, blood serum, sputum, spinal fluid, serous fluid from a pleural cavity, nipple aspirate, lymph, tracheolar fluid, intestinal juice, genitourinary tract fluid, breast milk, semen, peritoneal fluid, cystic tumor fluid, amniotic fluid, or any combination thereof.

4. The method of claim 1, wherein the vesicle is a microvesicle or an exosome.

5. The method of claim 1, further comprising:
measuring an amount of an integrin protein in the biological sample; and
comparing the amount of the integrin protein with a measured amount of an integrin protein in a control;
wherein providing a breast cancer diagnosis comprises determining if the measured amount of the microRNA and the integrin protein from the biological sample is greater or less than the measured amount of the microRNA and the integrin protein from the control,
wherein when the control is an amount of integrin and microRNA from a biological sample from a subject having no breast tumor or a benign breast tumor, an increased amount of microRNA and integrin protein from the biological sample relative to the control is indicative of breast cancer in the subject, and
wherein when the control is an amount of integrin and microRNA from a biological sample from a subject having breast cancer, an decreased amount of microRNA and integrin protein from the biological sample relative to the control is indicative of non-breast cancer in the subject.

6. The method of claim 5, wherein the integrin protein comprises an integrin α subunit, an integrin β subunit, or a combination thereof.

7. The method of claim 5, wherein the integrin protein comprises a polypeptide selected from the group consisting of CD49a, CD49b, CD49c, CD49d, CD49e, CD49f, integrin α 8 (ITGA8), integrin α 9 (ITGA9), integrin α 10 (ITGA10), integrin α 11 (ITGA11), CD11D, CD103, CD11a, CD11b, CD51, CD41, CD11c, CD29, CD18, CD61, CD104, integrin β 5 (ITGB5), integrin β 6 (ITGB6), integrin β 7 (ITGB7), and integrin β 8 (ITGB8).

8. The method of claim 1, wherein
hsa-miR-126 comprises the nucleotide sequence of SEQ ID NO: 1,
hsa-miR-23a comprises the nucleotide sequence of SEQ ID NO: 2,
hsa-miR-24 comprises the nucleotide sequence of SEQ ID NO: 3,
hsa-miR-19b comprises the nucleotide sequence of SEQ ID NO: 4,
hsa-miR-103 comprises the nucleotide sequence of SEQ ID NO: 5,
hsa-miR-142-3p comprises the nucleotide sequence of SEQ ID NO: 6,
hsa-miR-144 comprises the nucleotide sequence of SEQ ID NO: 7,
hsa-miR-15a comprises the nucleotide sequence of SEQ ID NO: 8,
hsa-miR-185 comprises the nucleotide sequence of SEQ ID NO: 9,
hsa-miR-93 comprises the nucleotide sequence of SEQ ID NO: 10, and
hsa-miR-30c comprises the nucleotide sequence of SEQ ID NO: 11.

9. The method of claim 1, wherein measuring the amount of miRNA comprises contacting the miRNA with a primer or probe for the miRNA.

10. The method of claim 9, wherein the method comprises measuring the amount of two or more miRNA selected from the group consisting of hsa-miR-126, hsa-miR-23a, hsa-miR-24, hsa-miR-19b, hsa-miR-103, hsa-miR-142-3p, hsa-miR-144, hsa-miR-15a, hsa-miR-185, and hsa-miR-93.

11. The method of claim 9, wherein the method comprises measuring the amount of five or more miRNA selected from hsa-miR-126, hsa-miR-23a, hsa-miR-24, hsa-miR-19b, hsa-miR-103, hsa-miR-142-3p, hsa-miR-144, hsa-miR-15a, hsa-miR-185, and hsa-miR-93.

12. The method of claim 9, wherein the method comprises measuring the amount of all of hsa-miR-126, hsa-miR-23a, hsa-miR-24, hsa-miR-19b, hsa-miR-103, hsa-miR-142-3p, hsa-miR-144, hsa-miR-15a, hsa-miR-185, and hsa-miR-93.

13. The method of claim 9, wherein the method further comprises measuring the amount of hsa-miR-30c.

* * * * *

SEQUENCE LISTING

<160> NUMBER OF SEQ ID NOS: 11

<210> SEQ ID NO 1
<211> LENGTH: 22
<212> TYPE: RNA
<213> ORGANISM: Artificial Sequence

```
<220> FEATURE:
<223> OTHER INFORMATION: Synthetic (hsa-miR-126)

<400> SEQUENCE: 1
ucguaccgug aguaauaaug cg                                              22

<210> SEQ ID NO 2
<211> LENGTH: 21
<212> TYPE: RNA
<213> ORGANISM: Artificial Sequence
<220> FEATURE:
<223> OTHER INFORMATION: Synthetic (hsa-miR-23a)

<400> SEQUENCE: 2
aucacauugc cagggauuuc c                                               21

<210> SEQ ID NO 3
<211> LENGTH: 22
<212> TYPE: RNA
<213> ORGANISM: Artificial Sequence
<220> FEATURE:
<223> OTHER INFORMATION: Synthetic (hsa-miR-24)

<400> SEQUENCE: 3
uggcucaguu cagcaggaac ag                                              22

<210> SEQ ID NO 4
<211> LENGTH: 23
<212> TYPE: RNA
<213> ORGANISM: Artificial Sequence
<220> FEATURE:
<223> OTHER INFORMATION: Synthetic (hsa-miR-19b)

<400> SEQUENCE: 4
ugugcaaauc caugcaaaac uga                                             23

<210> SEQ ID NO 5
<211> LENGTH: 23
<212> TYPE: RNA
<213> ORGANISM: Artificial Sequence
<220> FEATURE:
<223> OTHER INFORMATION: Synthetic (hsa-miR-103)

<400> SEQUENCE: 5
agcagcauug uacagggcua uga                                             23

<210> SEQ ID NO 6
<211> LENGTH: 23
<212> TYPE: RNA
<213> ORGANISM: Artificial Sequence
<220> FEATURE:
<223> OTHER INFORMATION: Synthetic (hsa-miR-142-3p)

<400> SEQUENCE: 6
uguaguguuu ccuacuuuau gga                                             23

<210> SEQ ID NO 7
<211> LENGTH: 20
<212> TYPE: RNA
<213> ORGANISM: Artificial Sequence
<220> FEATURE:
<223> OTHER INFORMATION: Synthetic (hsa-miR-144)

<400> SEQUENCE: 7
uacaguauag augauguacu                                                 20
```

```
<210> SEQ ID NO 8
<211> LENGTH: 22
<212> TYPE: RNA
<213> ORGANISM: Artificial Sequence
<220> FEATURE:
<223> OTHER INFORMATION: Synthetic (hsa-miR-15a)

<400> SEQUENCE: 8
uagcagcaca uaaugguuug ug                                              22

<210> SEQ ID NO 9
<211> LENGTH: 22
<212> TYPE: RNA
<213> ORGANISM: Artificial Sequence
<220> FEATURE:
<223> OTHER INFORMATION: Synthetic (hsa-miR-185)

<400> SEQUENCE: 9
uggagagaaa ggcaguuccu ga                                              22

<210> SEQ ID NO 10
<211> LENGTH: 23
<212> TYPE: RNA
<213> ORGANISM: Artificial Sequence
<220> FEATURE:
<223> OTHER INFORMATION: Synthetic (hsa-miR-93)

<400> SEQUENCE: 10
caaagugcug uucgugcagg uag                                             23

<210> SEQ ID NO 11
<211> LENGTH: 23
<212> TYPE: RNA
<213> ORGANISM: Artificial Sequence
<220> FEATURE:
<223> OTHER INFORMATION: Synthetic (hsa-miR-30c)

<400> SEQUENCE: 11
uguaaacauc cuacacucuc agc                                             23
```